United States Patent [19]

Cerwin et al.

[11] 4,413,727

[45] Nov. 8, 1983

[54] FOLDER RETAINER FOR SURGICAL SUTURES

[75] Inventors: Robert J. Cerwin, Pittstown; Marvin Alpern, Glen Ridge, both of N.J.

[73] Assignee: Ethicon Inc., Somerville, N.J.

[21] Appl. No.: 359,403

[22] Filed: Mar. 18, 1982

[51] Int. Cl.³ .............................................. A61B 17/06
[52] U.S. Cl. ................................... 206/63.3; 206/380; 229/33; 229/36; 229/44 R; 229/45 R
[58] Field of Search ..................... 206/63.3, 380, 480, 206/83.3, 382, 383; 229/33, 36, 44 R, 45 R

[56] References Cited

U.S. PATENT DOCUMENTS

| 4,151,913 | 5/1979 | Freitag | 206/63.3 |
| 4,253,563 | 3/1981 | Komarnycky | 206/63.3 |
| 4,254,862 | 3/1981 | Barratt | 206/63.3 |

Primary Examiner—Joseph Man-Fu Moy
Attorney, Agent, or Firm—Robert L. Minier

[57] ABSTRACT

A folder retainer for surgical sutures, particularly multi panel, folded paper retainers for pluralities of coiled sutures.

10 Claims, 13 Drawing Figures

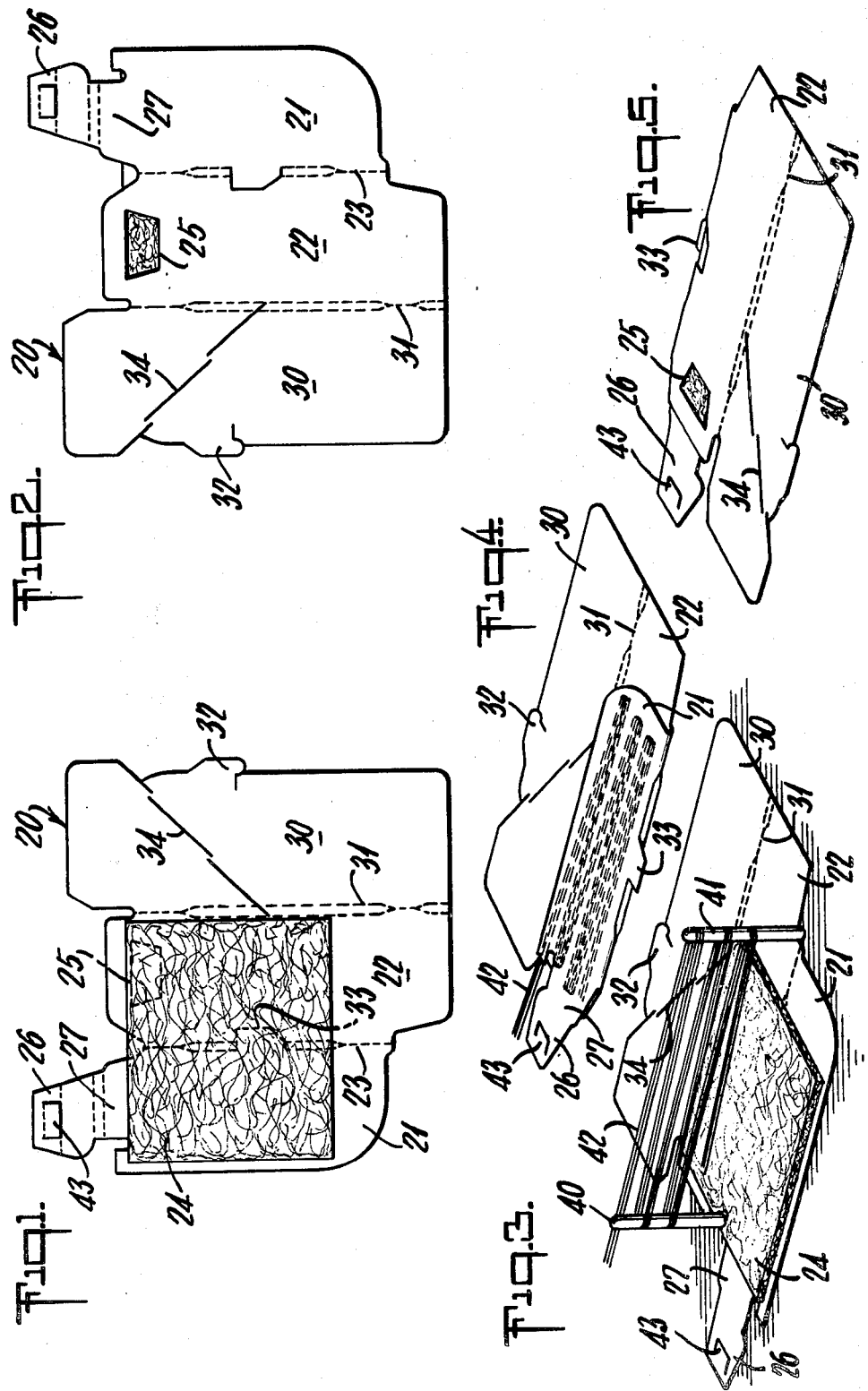

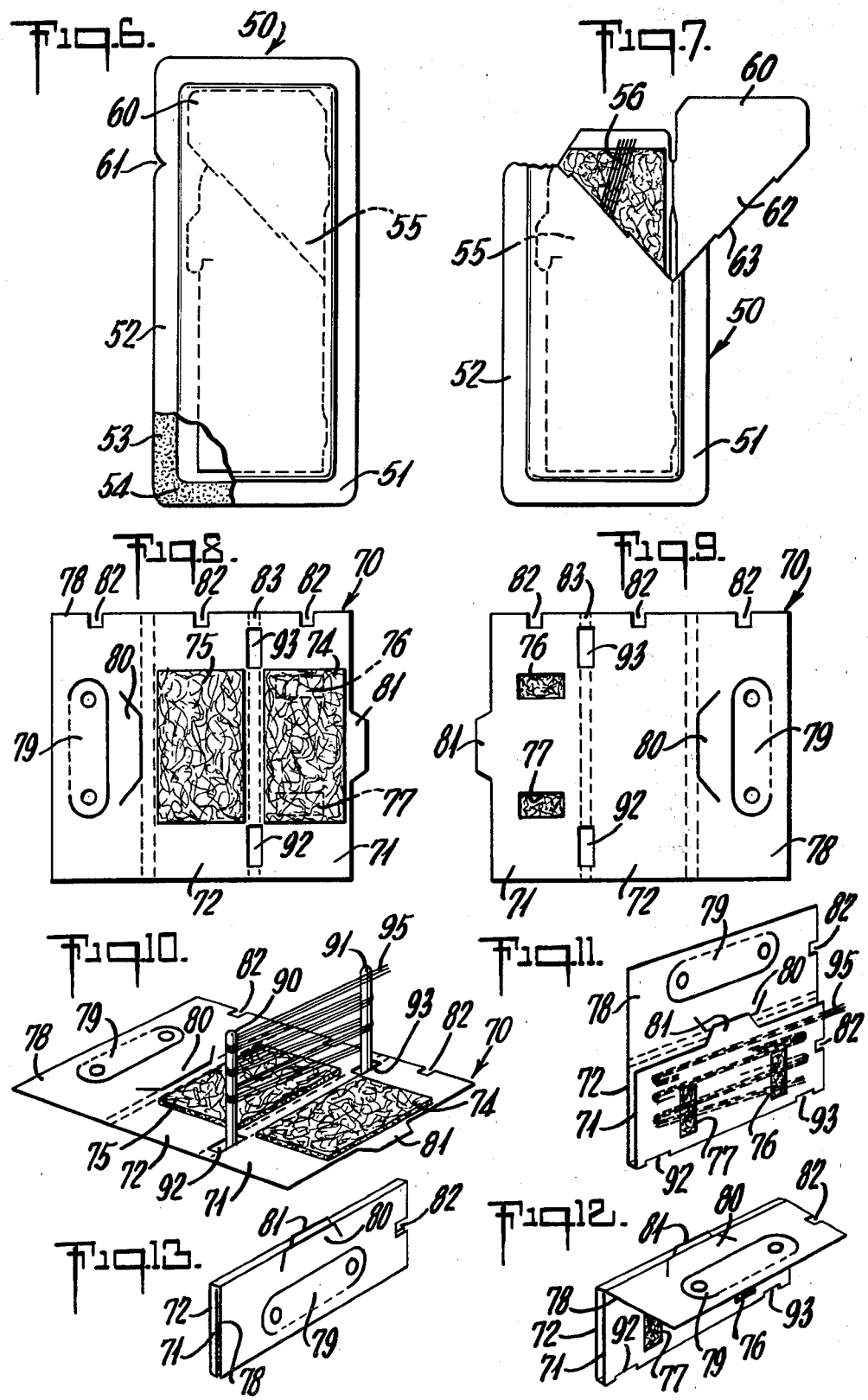

4,413,727

FOLDER RETAINER FOR SURGICAL SUTURES

BACKGROUND OF THE INVENTION

This invention relates to packages for surgical sutures and more particularly to a multi-panel, folded paper retainer for a plurality of coiled sutures.

Packages for surgical sutures are constructed according to the nature of the suture and its intended use. In general, the ideal package holds and protects the suture during storage and allows the sutures to be readily removed with a minimum of handling and difficulty. One specific package consists of a folded paper suture retainer contained in a sterile, hermetically sealed envelope. The sterility of the suture in the envelope is maintained by a second sealed overwrap. When the suture is about to be used, the outer wrap is opened in the operating room and the sealed envelope deposited in a sterile area. Sterile personnel thereupon tear open the envelope to gain access to the suture. A specific improved suture package which allows simplified access to the package is described in U.S. Pat. No. 3,939,696.

Also in many surgical procedures, the surgeon employs a large number of sutures and, hence, very often packages will be provided that contain multi strands of sutures. The major problem with multiple suture packages has been to provide a means for allowing individual sutures to be removed from the package without entanglement.

Recently, suture packages have been developed to retain a bundle of sutures in a pre-determined coiled configuration which permits individual sutures to be withdrawn from the package without entangling the remaining sutures. Such multi-strand packages with single strand access are illustrated in U.S. Pat. Nos. 4,089,409 and 4,126,221.

It is often difficult to manipulate these multi strand sutures and place them in the appropriate package and have them maintain a desired position until the package is fully closed and locked and the sutures held in place. The more resilient and flexible or springy the suture, the more difficult this operation becomes. One technique to assist in the manipulation of the suture materials is to face or place on the surfaces of the panels foam materials which have a high coefficient of friction and, hence, hold the suture in place and make it easier to handle when the individual is coiling and wrapping the suture.

What we have developed is an improved package preferably for use with multi strand sutures. Our new package simplifies and eases the coiling of the suture and the placing of the suture in the package and provides the appropriate locking of the adjacent panels to insure the sutures stay where placed at fast speeds and economically. Also, our improved retainer is economical in its construction and its manufacture.

SUMMARY OF THE PRESENT INVENTION

The present invention provides a folded retainer for surgical sutures. The retainer has first and second suture retainer panels foldably connected along one major edge thereof. A foam member is adhesively secured on opposed facing surfaces of the first and second panel. The adhesive is preferably a pressure sensitive adhesive and one of the panels includes a window which exposes the adhesive securing the foam member to the panel. A third panel is foldably connected to the panel not having the window and the third panel is foldable about the edge of the panel not having the window so as to contact the adhesive exposed in the window and lock the panels together.

In one embodiment of the present invention, the third panel is foldably connected along a minor edge of the panel not having the window and the third panel is foldable about the minor edge so as to contact the adhesive exposed in the window. A fourth panel is foldably connected along the other major edge of the second panel to overlie the first panel. The fourth and first panels include locking means to lock the unconnected edge of the fourth panel to the remaining panels to produce a folded retainer.

In preferred embodiments of the present invention, a portion of the panel that is to contact the exposed adhesive through the window is deflectable or depressible to improve the locking of the panel to the adhesive.

BRIEF DESCRIPTION OF THE DRAWINGS

The invention will be more fully described when taken in conjunction with the following drawings wherein:

FIG. 1 is a front plan view of an unfolded suture retainer of the present invention;

FIG. 2 is a back plan view of the unfolded suture retainer of FIG. 1;

FIG. 3 is a perspective view of the retainer of FIG. 1 positioned over suture winding pins with a suture being wound on the pins in a figure 8 pattern;

FIG. 4 is a perspective view of the package of FIG. 3 with the first and second panels folded together to lock the sutures in place just as the package is removed from the winding pins;

FIG. 5 is a perspective view of the folded suture retainer of FIG. 3 just prior to folding the third panel against the exposed adhesive and locking the fourth panel to the remaining panels;

FIG. 6 is a plan view of the completely folded suture retainer of FIG. 3 contained within a sealed outer envelope;

FIG. 7 is a plan view of the suture package and envelope of FIG. 6 opened to provide access to the sutures;

FIG. 8 is a front plan view of another embodiment of an unfolded suture retainer of the present invention;

FIG. 9 is a back plan view of the unfolded suture retainer of FIG. 8;

FIG. 10 is a perspective view of the retainer of FIG. 8 positioned over two suture winding pins with the sutures wound about the pins;

FIG. 11 is a perspective view of the package of FIG. 10 with the first and second panels folded with respect to each other to lock the sutures therebetween;

FIG. 12 is a perspective view with the third panel partially closed about the first and second panels; and FIG. 13 is a perspective view with the third panel fully closed about the first and second panels.

DETAILED DESCRIPTION OF THE PRESENT INVENTION

Referring to the drawings, in FIGS. 1 through 5, identical numerals are used for identical parts in each of these figures to aid in the description of the retainer. As seen in FIG. 1, the retainer 20 comprises first and second suture retaining panels 21 and 22 foldably connected along one major edge 23. Disposed on these panels, in faces which will abut each other on folding, is a foam member 24 for "parking" and frictionally securing the suture between the panels. The foam member may be secured to the panels by any suitable pressure-sensitive well known in the art. As may be more clearly seen in FIG. 2, there is a window or opening 25 disposed in the second suture retaining panel. The pressure-sensitive adhesive is exposed through the opening. A third panel 26 is foldably connected to a minor edge 27 of the first suture retainer panel, that is the panel not having the window opening. A fourth panel 30 is foldably connected along the other major edge 31 of the second suture retaining panel. The first suture retaining panel and the fourth panel include cooperating tab means 32 and 33 to lock the panels in place upon being folded as will be explained thereafter. Also, the fourth panel includes a diagnonal intermittently severed area 34 to allow for easy access to the ends of sutures as will also be hereinafter explained.

The packaging of the multiple sutures within the retainer will be more fully described in conjunction with FIGS. 3, 4, and 5. In FIG. 3, the suture retainer is placed over a set of winding pins 40 and 41. The first and second panels 21 and 22 of the retainer are disposed so that the foam member 24 sits between the pins. Multiple strands of sutures 42 are wound from pin to pin in a figure 8 configuration. Once the winding is completed, the ends of the sutures are allowed to extend beyond the pins. The first and second suture retaining panels 21 and 22 are then brought vertically upwards to encompass the sutures wound on the pins with the foam member encompassing opposite sides of the sutures. Once this is accomplished, the retainer with the sutures therein may be removed from the pins and the sutures are maintained in their wound or coiled configurations by engagement with the foam member 24. At this point, the third panel 26 is folded about the minor edge 27 of the first panel and pressed in adhesive engagement with the adhesive exposed through the window 25 in the second suture retaining panel. It is preferred that the third panel include a deflectable flap means 43 that can be depressed against the adhesive to provide more positive gripping between the panel and the adhesive. It is now a simple matter to put the remaining exposed suture ends down on top of the first suture panel 21 and then to fold the fourth panel 30 about the first panel entrapping the suture ends and allowing the tabs 33 and 32 on the first and fourth panels to lock to provide the retainer for the multiple strand sutures.

If desired, a window may also be placed in the retaining panel 21 behind the foam to expose adhesive through the window on the back of this panel. This exposed adhesive is used to assist in holding the forth panel 30 in place when folded about the first panel 21.

The suture retainers with the sutures therein may then be packaged and sterilized by various techniques as is well known in the art. In FIGS. 6 and 7, one specific package 50 is shown and is a conventional suture package formed by heat sealing the periphery 51 of the two panels 52 and 53 of aluminum foil coated on the interior surfaces thereof with a heat sealable polymeric composition 54. Other means for sealing may be employed as desired. Disposed within the envelope is a fully folded retainer 55 and multiple sutures 56 which have been sterilized and sealed within the envelope. A tab 60 projects slightly beyond the width of the folded retainer and is secured in the sealed area of the envelope. A tear notch 61 is provided in the outer edge of the envelope and located approximately at the lower edge of the tab to facilitate opening of the suture package when tearing the outer envelope. The suture package as illustrated in FIG. 6 is sterile and hermetically sealed and may be stored for extended periods of time. When the sutures are to be removed from the package, the outer envelope is opened by tearing at the notch as illustrated in FIG. 7. Since the tab is secured at the seal line of the envelope about the notch, the fourth panel 62 is simultaneously torn as the envelope is opened. The fourth panel is made to tear diagonally across the width of the suture package guided by the edge of the die cut portion 63. This tearing exposes the ends of the multiple sutures 56 and it is a simple matter to remove the individual sutures from the package.

In FIGS. 8 through 13 there is shown another embodiment of a new and improved suture retainer. Again, to aid in the description and for the sake of clarity, the same numbers have been used for identical parts in FIGS. 8 through 13. In this embodiment, as shown in FIGS. 8 and 9, the suture retainer 70 comprises three panels. The first and second suture retainer panels 71 and 72 are foldably connected along the major edge 73 thereof. The major edge 73 comprises a pair of fold lines which form a narrow area 83 between panels 71 and 72. Openings 92 and 93 are disposed in this narrow area. These openings are used to assist in placing the sutures in the retainer as will be explained in conjunction with FIGS. 10 to 13. Disposed on each of these panels 71 and 72 is a foam "parking" member 74 and 75 or a foam securing member. In this embodiment, the foam members are separated rather than them being connected as in the previous embodiment described. The foam member is secured to the panels by suitable pressure-sensitive adhesive and in the first suture holding panel 71 there are provided two openings or windows 76 and 77 to allow the adhesive to be exposed through the back of the panel as is more clearly shown in FIG. 9. Foldably connected along the other major edge 74 (which also comprises two parallel closely spaced fold lines) 72 is a third panel 78. This panel 78 includes a deflectable flap means 79 for use in securing the folded panel as will be described hereinafter. This panel 78 also includes a slit 80 to accept the tab 81 exposed on the first suture retaining panel 71 for use as will be more fully described in conjunction with FIGS. 10 through 13 on the folding of the suture retainer. Notches 82 are provided at the upper edge of each of the panels to provide for suture ends to overlap from one panel to another panel.

Referring to FIGS. 10 through 13, in producing a suture package, the retainer 70 is disposed on pins 90 and 91 which are allowed to protrude through the openings 92 and 93 in the panel area between the first and second retaining panels 71 and 72 and between the foam holding members 76 and 77. A plurality of suitable sutures 94 are wound in a coil like manner between the pins with the ends of the sutures 95 allowed to extend beyond the pins. Once the sutures are wound about the pins, the suture retaining panels 71 and 72 are brought together while the sutures are still on the pins so that the foam members are disposed facing each other and in engagement with the suture to hold the sutures in place. The disposed ends of the sutures are folded around the notch 82 in the first panel and the third panel 78 is folded about the major edge of the second panel 72 to be disposed on top of the first panel. At this point, the tab 81 of the first panel is inserted into the slit 80 between the third and second panel to lock the panels together and the third panel is brought in face to face relationship with the first panel.

The third panel is disposed on the first suture retainer panel and the deflectable flap means 79 is depressed so that it engages the adhesive exposed through the windows 76 and 77 of the suture retaining panel 71 to lock the sutures in place. The suture retainer is packaged in conventional envelopes which are sterile and hermetically sealed. In use, it is a simple matter to remove the suture retainer from the sealed sterile envelope and remove the adhesively secured third panel from the first panel to expose the suture ends to allow removal of individual suture strands from the retainer.

The suture retainer of the present invention is constructed of a heavy weight, relatively stiff paper or paper board such as 5 to 12 point solid bleached sulfate board. The paper board is foldable and yet sufficiently strong and stiff to support the suture and provide relatively rigid packages. Similar materials including plastic, foils and laminates, of these with each other or with paper can also be used with good results. The suture folder can be readily cut from such materials by a single die which also forms the desired fold lines including the necessary gussets in accordance with the present invention.

The foam member may be made from any of the standard foam materials such as the polyethers, polyesters, and the like. The foam sheets are usually less than ⅛ inch thick and cover a major portion of the surfaces on the opposed retainer panels. The foams may be secured to the panels by any of the pressure-sensitive adhesives well known in the art which may be applied to the surface of the foam and the foam secured to the panels.

Sutures packaged in three to eight strands or more may be individually removed from the packages of the present invention by simply grasping an exposed end of a single suture and withdrawing the suture with a steady pull.

Sutures packaged in accordance with the present invention may be multi filament or mono filament sutures and multi filament sutures may be braided, twisted, or covered. In addition, the sutures may be packaged with or without needles attached to the end of the suture.

The preceding description has been directed primarily to preferred embodiments of the present invention and many variations which nevertheless employ the essential features thereof will be apparent to those skilled in the art. For example, while the foregoing has described a folder to be employed with vertical winding pins, the suture may be coiled and positioned within the package by any convenient means which will permit single strand delivery from the folded package. Thus, the winding pins may be omitted in certain cases or other structures may be added if required by the intended folder loading method. These and other variations are accordingly included within the scope of the present invention.

What is claimed is:

1. A folded retainer for surgical sutures comprising:
    (a) first and second suture retaining panels foldably connected along one major edge thereof,
    (b) a foam member adhesively secured on facing surfaces of said first and second panels;
    (c) one of said first and second panels including a window exposing said adhesive securing the foam to said panel; and
    (d) a third panel foldably connected to an edge of the panel not having the window, said third panel being foldable about said edge so as to contact the adhesive exposed in said window.

2. The folded retainer for surgical sutures comprising:
    (a) first and second suture retaining panels foldably connected along one major edge thereof;
    (b) a foam member adhesively secured on facing surfaces of said first and second panels;
    (c) one of said first and second panels including at least one window exposing adhesive securing the foam to the panel;
    (d) a third panel foldably connected along a minor edge of the panel not having the window, said third panel being foldable about said edge so as to contact the adhesive exposed in said window; and
    (e) a fourth panel foldably connected to the other major edge of said second panel so as to overlie said first panel in its folded configuration.

3. A retainer of claim 2 having integral locking means to secure said retainer in its folded configuration.

4. A retainer of claim 3 wherein the integral locking means are interlocking tabs disposed at one major edge of the fourth panel and at the major edge where the first and second panels are connected.

5. A folded retainer according to claims, 2, 3, or 4 wherein the third panel includes a depressible flap means for contacting exposed adhesive in the window.

6. A retainer of claim 2 including dual parallel fold lines between said first and second and said second and fourth panels.

7. A retainer of claim 6 including openings for suture winding pins within the parallel fold lines between the said first and second panels.

8. A suture package comprising in combination a folded retainer of claim 2, 3, or 4 and a plurality of sutures positioned between said first and second panels, said suture package enclosed in an outer envelope sealed around the periphery thereof.

9. A suture package of claim 8 wherein said sutures are collated into a bundle of substantially aligned strands and coiled between said first and second panels in a figure 8 configuration.

10. A folded retainer according to claims 2, 3 or 4 wherein the foam members are separate pieces of foam, one attached to said first panel and a second attached to said second panel and disposed so that on closing the foam members face each other.

* * * * *